US010080875B2

(12) United States Patent
Argentine et al.

(10) Patent No.: US 10,080,875 B2
(45) Date of Patent: Sep. 25, 2018

(54) HANDLE COMPONENT FOR PROVIDING A PRESSURIZED MATERIAL

(71) Applicant: Medtronic Vascular, Inc., Santa Rosa, CA (US)

(72) Inventors: Jeffery Argentine, Petaluma, CA (US); Samuel Robaina, Novato, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 173 days.

(21) Appl. No.: 14/955,384

(22) Filed: Dec. 1, 2015

(65) Prior Publication Data

US 2017/0151422 A1    Jun. 1, 2017

(51) Int. Cl.
| | |
|---|---|
| A61M 25/10 | (2013.01) |
| A61M 39/10 | (2006.01) |
| A61B 17/12 | (2006.01) |
| A61F 2/958 | (2013.01) |
| A61B 17/22 | (2006.01) |

(52) U.S. Cl.
CPC . *A61M 25/10185* (2013.11); *A61B 17/12113* (2013.01); *A61B 17/12186* (2013.01); *A61F 2/958* (2013.01); *A61M 25/104* (2013.01); *A61M 25/10182* (2013.11); *A61M 39/105* (2013.01); *A61B 2017/1205* (2013.01); *A61B 2017/22001* (2013.01); *A61B 2017/22062* (2013.01); *A61B 2017/22069* (2013.01); *A61M 2025/109* (2013.01); *A61M 2205/583* (2013.01)

(58) Field of Classification Search
CPC ...... A61M 25/10182; A61M 25/10185; A61M 5/315; A61M 5/31501; A61B 17/12186; A61B 2017/22062
See application file for complete search history.

(56) References Cited

U.S. PATENT DOCUMENTS 5,324,260 A * 6/1994 O'Neill ............. A61M 25/0023
604/103.08
5,342,304 A    8/1994 Tacklind et al.
(Continued)

FOREIGN PATENT DOCUMENTS

| WO | WO2005/115524 | 12/2005 |
| WO | WO2009/132309 | 10/2009 |

OTHER PUBLICATIONS

PCT/US2016/064107, The International Search Report and the Written Opinion of the International Searching Authority, dated Mar. 8, 2017.
(Continued)

*Primary Examiner* — Laura Bouchelle
*Assistant Examiner* — Tasnim M Ahmed
(74) *Attorney, Agent, or Firm* — Medler Ferro Woodhouse & Mills PLLC (57) ABSTRACT

A handle component of a medical device is disclosed for delivering a material to an enclosed cavity or space. The handle component includes a self-contained mechanism for holding the material and for providing or releasing the material to the enclosed cavity. The handle component also includes a pressure relief valve in fluid communication with the mechanism and the enclosed cavity. The pressure relief valve is configured to indicate when delivery of the material to the enclosed cavity reaches a preselected or set pressure and to thereby assure precise filling of the enclosed cavity with the material.

20 Claims, 7 Drawing Sheets

(56) References Cited

U.S. PATENT DOCUMENTS

| | | | |
|---|---|---|---|
| 5,647,847 A * | 7/1997 | Lafontaine | A61M 25/10185 604/100.03 |
| 5,860,955 A * | 1/1999 | Wright | A61M 25/1018 604/98.01 |
| 8,021,330 B2 | 9/2011 | McAndrew | |
| 8,636,715 B2 | 1/2014 | Patel | |
| 2005/0267407 A1 | 12/2005 | Goldman | |
| 2008/0103477 A1* | 5/2008 | Jones | A61B 17/12022 604/508 |
| 2011/0144677 A1 | 6/2011 | Ward et al. | |
| 2014/0214057 A1 | 7/2014 | Piccagli | |
| 2015/0005706 A1* | 1/2015 | Diaz | A61M 5/3221 604/110 |
| 2015/0032142 A1 | 1/2015 | Silvestro | |
| 2015/0231378 A1* | 8/2015 | Pepper | A61M 29/02 606/194 |

OTHER PUBLICATIONS

U.S. Appl. No. 14/877,351, filed Oct. 7, 2015, Massimo et al.

* cited by examiner

HANDLE COMPONENT FOR PROVIDING A PRESSURIZED MATERIAL

FIELD OF THE INVENTION

The invention relates generally to a handle component for providing a pressurized material to a medical device, such as a stabilization or dilatation balloon, or for providing a pressurized material to an enclosed cavity or space during a medical procedure, such as delivering a substance within an aneurysm in vivo.

BACKGROUND OF THE INVENTION

Many medical device and medical procedures require use of a pressurized material that is to be introduced until a certain or preselected pressure is reached. For instance, a balloon catheter having a stabilization balloon for anchoring and stabilizing an occlusion bypassing device within a wall of a vessel requires an inflation fluid to be introduced at a fairly low pressure as is known to one of ordinary skill in the art. Such catheters and their use in crossing or bypassing a CTO have been described, for example, in U.S. Pat. No. 8,021,330 to McAndrew and U.S. Patent Application Publication No. 2015/0032142 A1 to Silvestro, each of which is incorporated by reference herein in its entirety. Another example is a dilatation balloon of a delivery catheter for implanting a balloon-expandable stent within the vasculature or another body lumen. An inflation fluid must be introduced to attain a certain pressure within the dilatation balloon that will properly expand the stent without over-expanding the stent and/or injuring the vessel or body lumen. As well, it is known to introduce a paving material, such as biocompatible foam, into an aneurysm in order to fill the aneurysm and promote healing. In such a medical procedure, the paving material must be introduced at a certain pressure in order to prevent rupture of the aneurysm.

Each of the foregoing medical device and procedures faces challenges to assure proper pressures are achieved and to avoid over-pressurization. Often such medical device and procedures require the use of expensive inflation and/or pressure monitoring equipment, such as an ENDO-FLATER® and/or pressure gauges. Accordingly, a need in the art exists for a simpler and less expensive inflation fluid, or other material, delivery mechanism that can consistently, safely, and accurately inflate a balloon thereof or provide a material to an enclosed cavity or space at a suitable pressure.

BRIEF SUMMARY OF THE INVENTION

Embodiments hereof are directed to a handle component of a medical device for delivering a material to an enclosed cavity. The handle component includes a self-contained mechanism for holding the material and for providing or releasing the material to the enclosed cavity. The handle component also includes a pressure relief valve in fluid communication with the mechanism and the enclosed cavity. The pressure relief valve is configured to indicate when delivery of the material to the enclosed cavity reaches a preselected pressure.

In an embodiment, a balloon catheter may include the handle component, the material may be an inflation fluid and the enclosed cavity may be a balloon of the balloon catheter. In such an embodiment, the mechanism of the handle component may be in fluid communication with a lumen of the balloon catheter, wherein the lumen is in fluid communication with the balloon. In an embodiment, the mechanism of the handle component may include a syringe that contains the inflation fluid for inflating the balloon to the preselected pressure when a plunger of the syringe is depressed. In such an embodiment, the mechanism of the handle component may further include an actuation cap coupled to a head of the plunger of the syringe and threadably engaged with the handle component when the mechanism is in a locked configuration. In such an embodiment, the mechanism of the handle component may have an unlocked configuration in which the actuation cap may be configured to be distally advanced relative to the handle component and to thereby simultaneously depress the plunger of the syringe to release the inflation fluid therefrom for inflating the balloon. In such an embodiment, the mechanism of the handle component may have an unlocked configuration in which the actuation cap may be configured to be proximally retracted relative to the handle component and to thereby simultaneously retract the plunger of the syringe to remove the inflation fluid and deflate the balloon.

In an embodiment, a delivery catheter may include the handle component, the material may be a biocompatible foam and the enclosed cavity may be an aneurysm. In such an embodiment, the mechanism of the handle component may be in fluid communication with a lumen of the delivery catheter, and the lumen may be configured to be in fluid communication with the aneurysm when the delivery catheter is deployed in vivo. In an embodiment, the mechanism of the handle component may include a syringe that contains the foam for filling the aneurysm to the preselected pressure when a plunger of the syringe is depressed.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. The term "shape memory" is used in the following description with reference to a needle component hereof and is intended to convey that the structure is shaped or formed from a material that can be provided with a mechanical memory to return the structure from a straightened delivery configuration to an angled or bent deployed configuration. Non-exhaustive exemplary materials that may be imparted with a shape memory include stainless steel, a pseudo-elastic metal such as a nickel titanium alloy or nitinol, or a so-called super alloy, which may have a base metal of nickel, cobalt, chromium, or other metal. Shape memory may be imparted to a tubular or rod-like structure by thermal treatment to achieve a spring temper in stainless steel, for example, or to set a mechanical memory in a susceptible metal alloy, such as nitinol.

The following detailed description is merely exemplary in nature and is not intended to limit the invention or the application and uses of the invention. Although the majority of the description of the invention is in the context of using a balloon catheter in the treatment of occluded blood vessels such as smaller diameter peripheral or coronary arteries, the invention may also be implemented in balloon catheters used in any other body passageway and for performing other medical procedures, such as "angioplasty" or "PTA," or "PTCA" when performed in the coronary arteries, and such as deploying a balloon-expandable stent anywhere in the vasculature. The invention may also be implemented in a medical device that is used in a medical application in which a pressure of a material for filling any cavity or enclosed space must be controlled, such as a medical device used to supply a material for filling an aneurysm. Furthermore, there is no intention to be bound by any expressed or implied theory presented in the preceding technical field, background, brief summary or the following detailed description.

Figure 1:
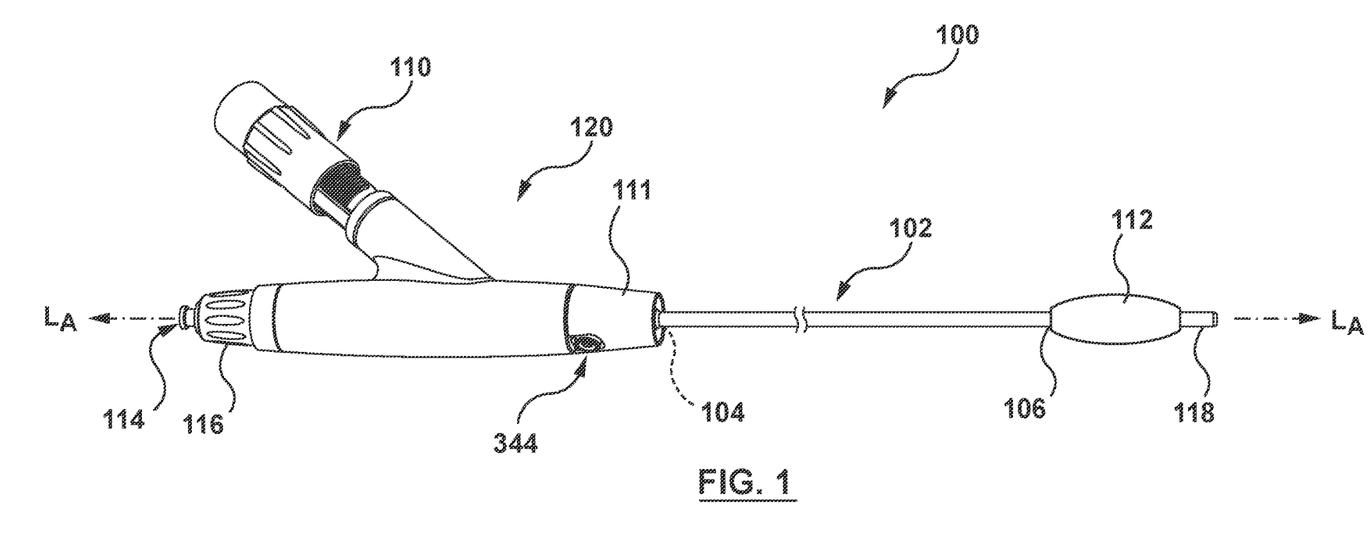
FIG. 1 is a side view of a balloon catheter with a handle component in accordance with an embodiment hereof.

A handle component 120 in accordance with an embodiment hereof is depicted in FIG. 1 as a component of a balloon catheter 100 that may be used to subintimally bypass an occlusion in a blood vessel such as a chronic total occlusion (CTO) of an artery. In the embodiment of FIG. 1 the balloon catheter 100 includes, a shaft component 102, a balloon 112, and an atraumatic tip component 118. The handle component 120 in accordance with an embodiment hereof is operably attached to the shaft component 102, the balloon 112 and a needle component 230 shown in FIG. 2, wherein the needle component 230 is used to re-enter a true lumen of a vessel distal of the CTO. The handle component 120 is described and illustrated in greater detail below with reference to FIGS. 3 through 6; however as shown in FIG. 1, the handle component 120 includes a self-contained inflation mechanism 110 for providing an inflation fluid to the balloon 112, a proximal port 114 for permitting insertion of a guidewire (not shown), a rotatable proximal knob 116 for advancing and retracting the needle component 230, and a rotatable distal knob 111 for rotating the shaft component 102 and balloon 112 that is fixed thereto.

Figure 2:
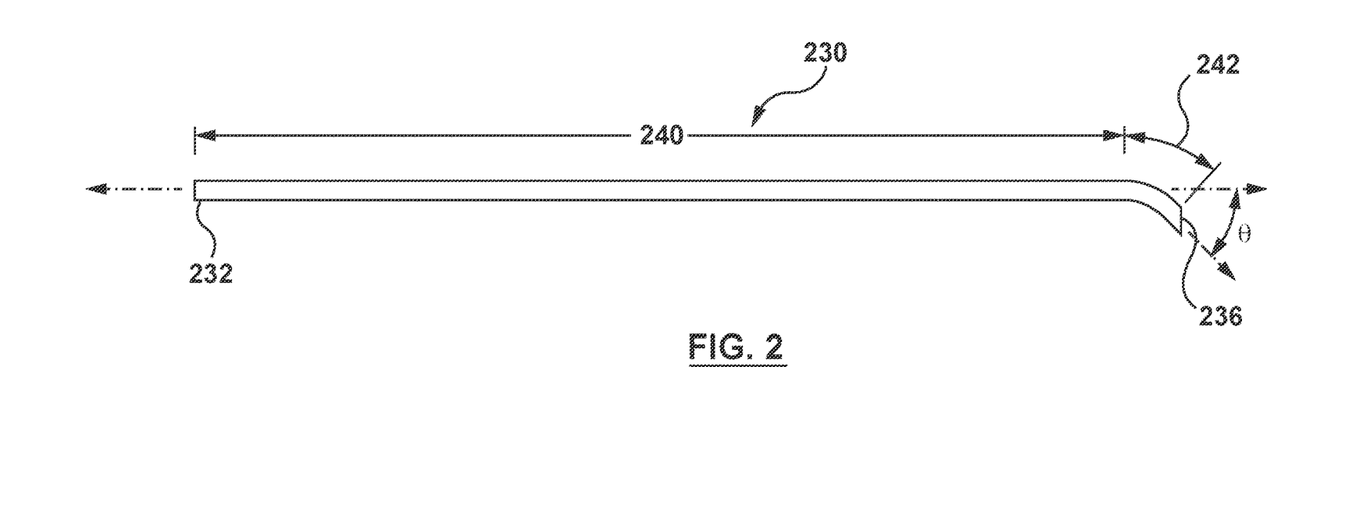
FIG. 2 is a side view of a needle component for use with the balloon catheter of FIG. 1 when the balloon catheter is used as an occlusion bypassing apparatus in accordance with an embodiment hereof.
Figure 3:
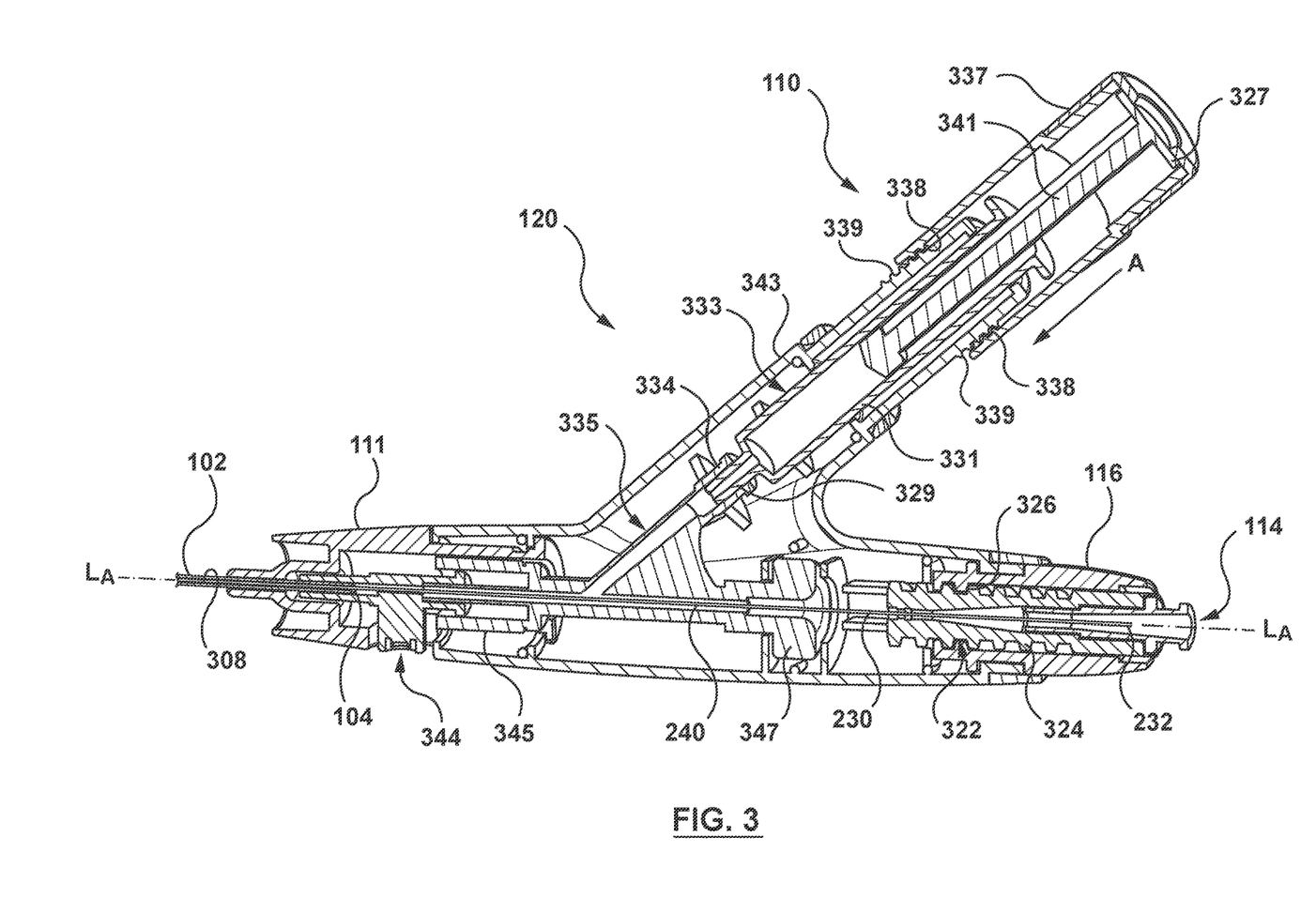
FIG. 3 is a sectional view of the handle component of FIG. 1 in accordance with an embodiment hereof.

The shaft component 102 defines a lumen 308, as shown in FIG. 3, from a proximal end 104 to a distal end 106 thereof that provides fluid communication between the handle component 120 and the balloon 112 for directing the inflation fluid thereto, as would be understood by one of skill in the art. In an embodiment, the proximal portion of the shaft component 102 is secured to the rotatable distal knob 111 of the handle component 120 in order to be rotated about its longitudinal axis $L_A$ thereby. In an embodiment, lumen 308 of the shaft component 102 is sized to accommodate the needle component 230, which is shown removed from the balloon catheter 100 in FIG. 2 for illustrative purposes only. In an embodiment, the needle component 230 may be longitudinally advanced within the lumen 308 of the shaft component 102 by manipulating the rotatable proximal knob 116 of the handle component 120, as described in detail below. The shaft component 102 may be formed of one or more polymeric materials, non-exhaustive examples of which include polyethylene terephthalate (PET), polypropylene, polyethylene, polyether block amide copolymer (PEBAX), polyamide, fluoropolymers, and/or combinations thereof, either laminated, blended or co-extruded. Optionally, shaft component 102 or some portion thereof may be formed as a composite having a reinforcement layer incorporated within a polymeric body in order to enhance strength and/or flexibility. Suitable reinforcement layers include braiding, wire mesh layers, embedded axial wires, embedded helical or circumferential wires, hypotubes, and the like. As well other types of construction are also suitable for the shaft component 102, such as, without limitation thereto, a catheter shaft formed by extrusion to have a multi-lumen profile such that a lumen is provided for accommodating the needle component 230 and a separate inflation lumen is provided for directing an inflation fluid to the balloon 112.

In accordance with embodiments hereof, the balloon 112 may have a symmetric or an asymmetric expanded configuration relative to a longitudinal axis $L_A$ of the balloon catheter 100, as may be suitable for use in anchoring and stabilizing the catheter within a subintimal space. In accordance with embodiments hereof, the balloon 112 may be formed of any suitable polymeric material used for dilatation balloon manufacturing, for instance, polyether block amide (PEBA) and polyurethane (PU), and may have an outer diameter in the range of 2-4 mm and a length in the range of 5-15 mm. Balloon 112 may be coupled to the shaft component 102 and the atraumatic tip component 118 by any suitable means known to one of ordinary skill in the art.

In an embodiment, the needle component 230 may be configured to be slidably disposed within the lumen 308 of the shaft component 102 and may define a lumen that extends from a proximal end 232 to a distal end 236 thereof for receiving a guidewire (not shown) therethrough. Needle component 230 may have an elongated segment 240 and an angled distal segment 242, as shown in FIG. 2. In embodiments in accordance herewith, the distal segment 242 may have an angle, bent or curved configuration that extends, bends, or otherwise curves at an acute angle θ relative to the elongated segment 240 and relative to the longitudinal axis $L_A$ of the balloon catheter 100. In embodiments hereof, angle θ may be in the range of 30° to 80°. In another embodiment, a needle component suitable for use in embodiments hereof may not have a preformed bend at its distal end but instead may bend as it is pushed free from a side port of the balloon catheter, as shown in U.S. Pat. No. 8,636,715 to Patel, which is incorporated by reference herein in its entirety.

In an embodiment hereof, the needle component 230 may be formed of a biocompatible resilient metal such as spring temper stainless steel or nitinol, which utilizes the elastic properties of stress induced martensite, such that a heat or thermal treatment of the selected material may be used to provide a shape set or shape memory to the distal segment 242. Accordingly, the distal segment 242 of the needle component 230 may be held in a straightened configuration when housed within the shaft component 102, and/or within a distal length of the balloon catheter 100, and will resume an angled configuration when distally advanced from the tip component 118. In another embodiment, the needle component 230 may be a hypotube of spring temper stainless steel or nitinol with a distal end that has been shape set in the angled configuration to form the angled distal segment 242. In another embodiment, the needle component 230 may be formed from more than one material, e.g., with the elongated segment 240 being formed of stainless steel and only the angled distal segment 242 being formed of nitinol to have a shape memory. In another embodiment, the needle component 230 may be formed of a biocompatible resilient metal and may have flexibility at its distal end that causes the needle component to bend as it exits a side port of the catheter, as shown in U.S. Pat. No. 8,636,715 to Patel.

Balloon catheters and components thereof, and needle components and features thereof that may be adapted for use with a handle component in accordance with embodiments hereof and for use as occlusion bypassing apparatus in accordance herewith are disclosed in U.S. Patent Application Publication No. 2015/0032142 A1 to Silvestro and U.S. Pat. No. 8,636,715 to Patel, which were previously incorporated by reference above, as well as in U.S. Patent Application Publication No. 2014/0214057 to Piccagli, U.S. Patent Application Publication No. 2011/0144677 to Ward et al., and in U.S. application Ser. No. 14/877,351, filed Oct. 7, 2015, to Massimo et al., each of which is incorporated by reference herein in its entirety.

With reference to FIG. 3 that depicts a sectional view of the handle component 120, the proximal end 232 of the needle component 230 is secured to the proximal port 114 of the handle component 120. In the embodiment of FIG. 3, the proximal port 114 is in turn secured within a transmission member 322 that includes female threads 324 for mating with male threads 326 of the rotatable knob 116. The female and male threads 324, 326 of the transmission member 322 and the proximal knob 116, respectively, are configured to interact such that rotation of the proximal knob 116 in a first direction longitudinally advances the transmission member 322, as well as the proximal port 114 and the needle component 230, in a distal direction, and such that rotation of the proximal knob 116 in a second, opposite direction longitudinally retracts the transmission member 322, as well as the proximal port 114 and the needle component 230, in a proximal direction. In an embodiment, rotation of the proximal knob 116 in the first direction provides sufficient movement of the needle component 132 in the distal direction to position the distal segment 242 distal of the tip component 118, such that the distal segment 242 is able to resume its angled configuration.

Figure 4:
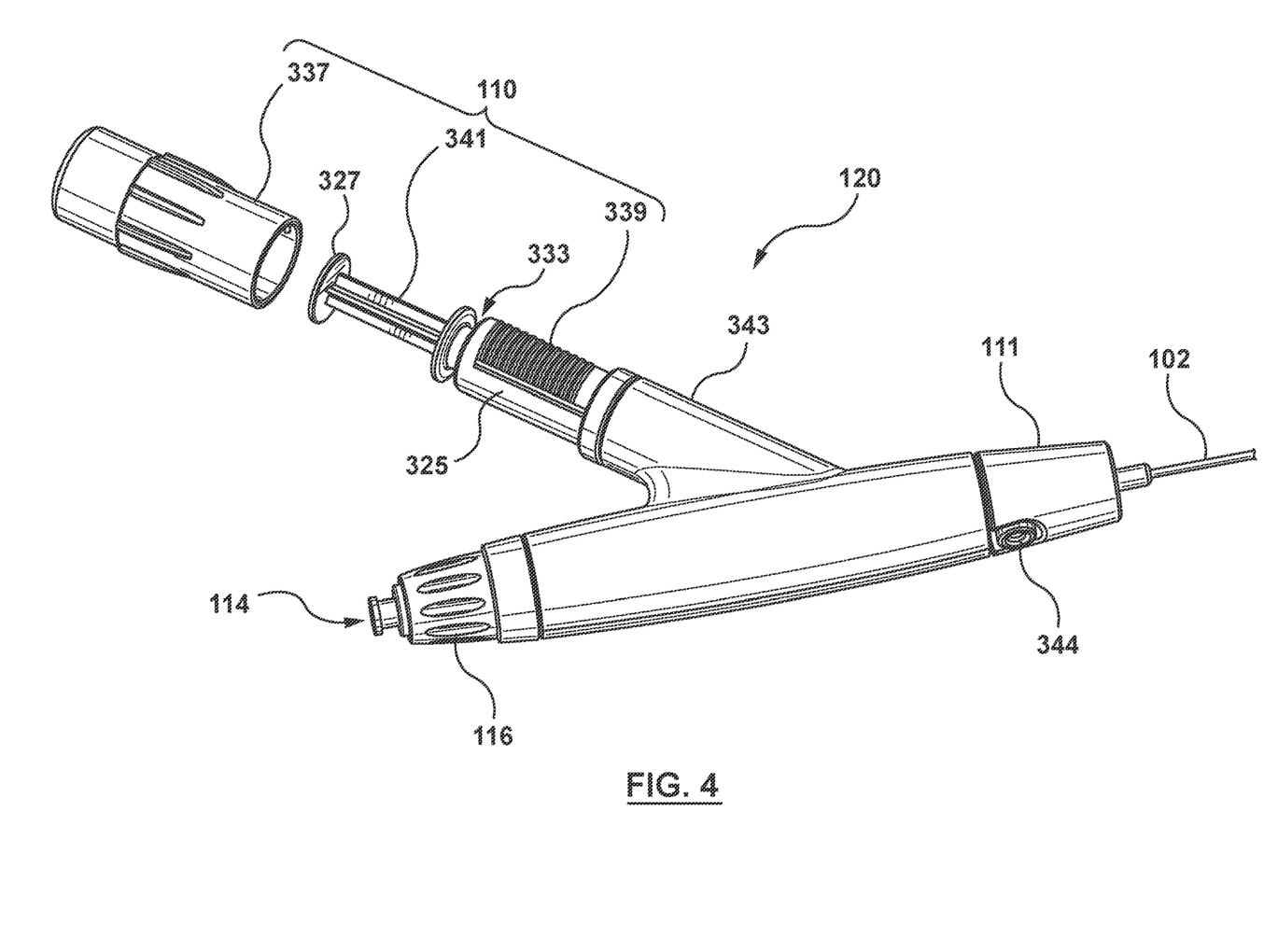
FIG. 4 is a perspective side view of a portion of the handle component of FIG. 1 shown with a threadable actuation cap detached therefrom to expose a syringe.
Figure 5:
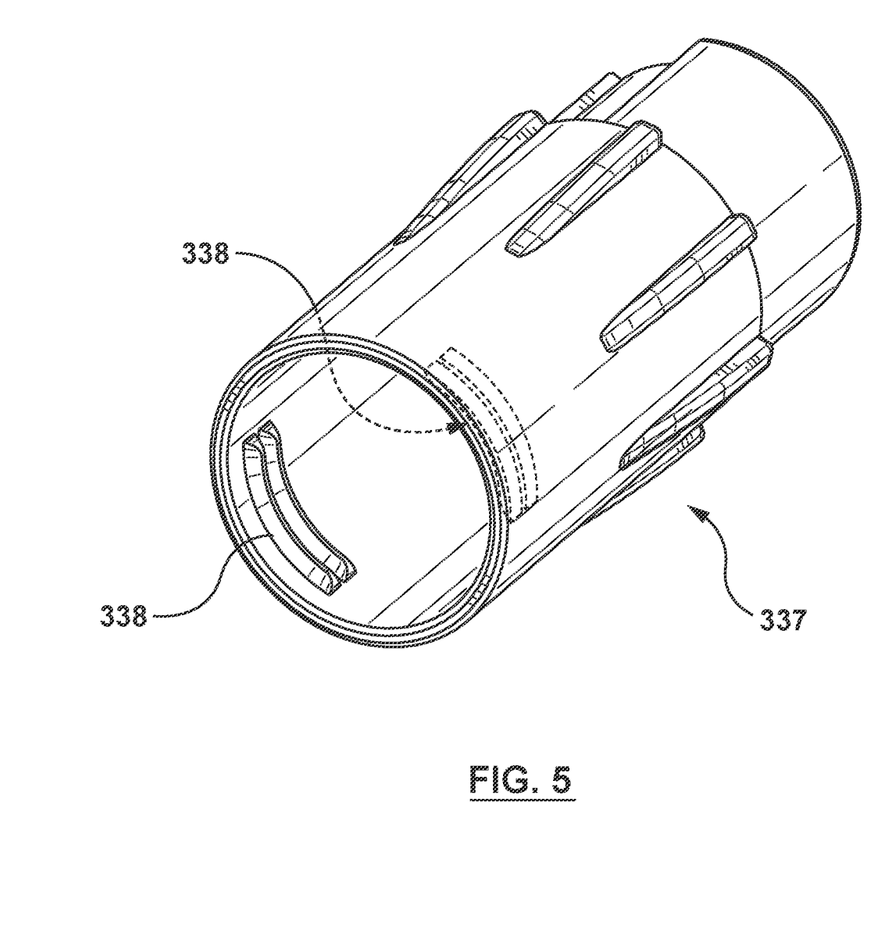
FIG. 5 is a perspective end view of the actuation cap separated from the handle component in accordance with an embodiment hereof.
Figure 6:
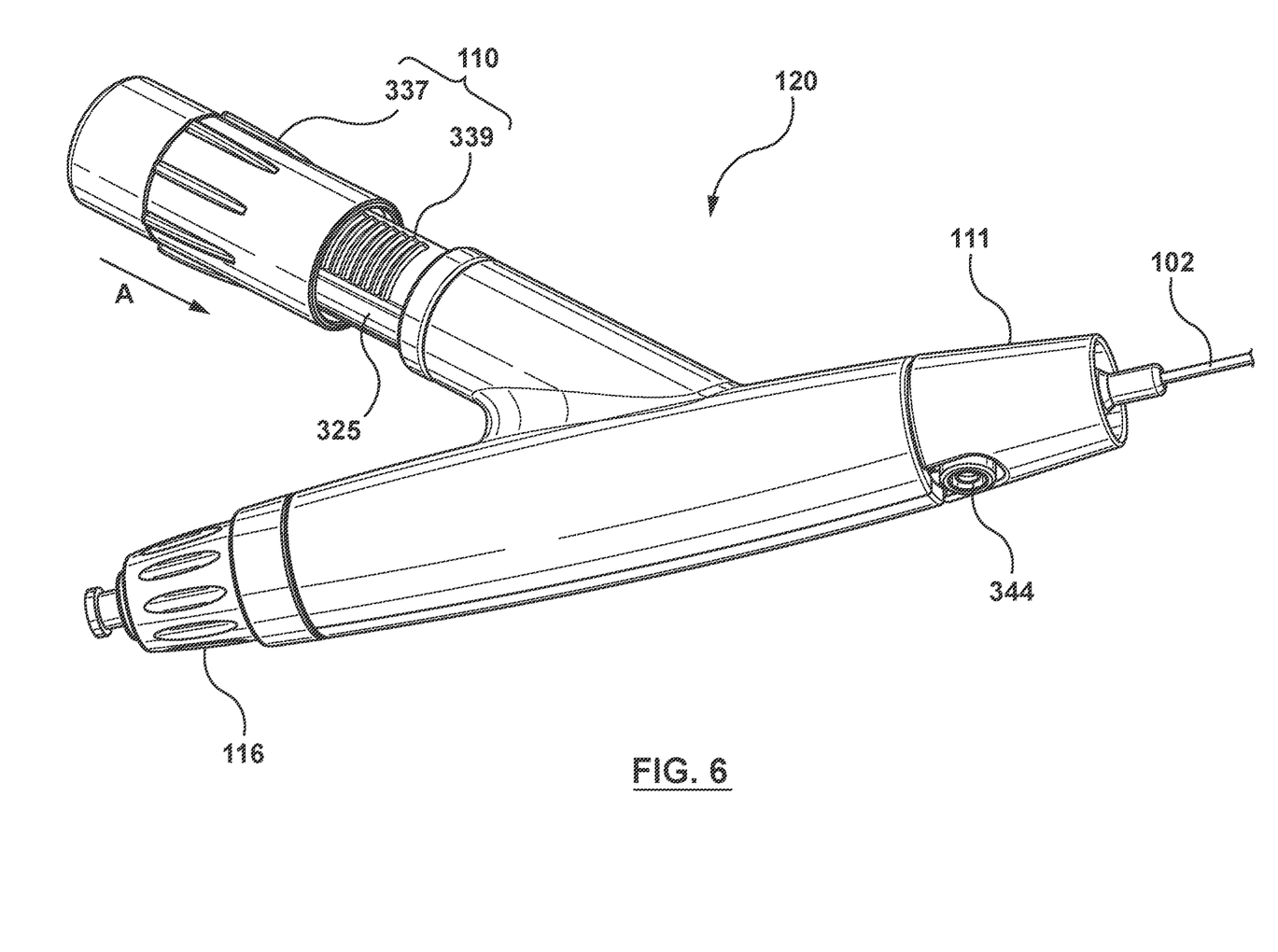
FIG. 6 is a perspective side view of the handle component in accordance with an embodiment hereof, shown with the actuation cap engaged over the syringe.

Components of the self-contained inflation mechanism 110 will now be described with reference to the sectional view of the handle component 120 shown in FIG. 3, the exploded view of the inflation mechanism 110 shown in FIG. 4, and with reference to FIGS. 5 and 6. In the embodiment of FIGS. 3-6, the inflation mechanism 110 includes an actuation cap 337 and a syringe 333 having a barrel 331 and a plunger 341. An extension 343 of the handle component 120 is configured to slidably receive the syringe barrel 331 such that a tip 329 of the syringe 332 may be mated with a first proximal fitting 334 of a three-way connector 335, which is positioned within the handle component 120 as described in greater detail below. For use in embodiments hereof, the syringe 333 may be any conventional syringe having a volume that is approximately twice the volume necessary to inflate the balloon 112. The excess is necessary for the expected losses due to the pressure relief valve 344 and having suitable dimensions for insertion with the handle component 120. In a particular embodiment, a syringe such as a Monojet 3 ml is suitable for use herewith. In accordance with embodiments hereof, the balloon 112 may be inflated to a preselected or predetermined pressure of between 0.1 atmospheres (ATM) and 20 atmospheres (ATM). In an embodiment, the preselected pressure may be three atmospheres pressure. In accordance with embodiments hereof, a syringe 333 may be an inexpensive polymeric syringe that is readily and cost-effectively replaceable.

The actuation cap 337 of the inflation mechanism 110 is configured to securely receive a head 327 of the syringe plunger 341. When the inflation mechanism 110 is in an unlocked configuration, the actuation cap 337 may be depressed or distally advanced relative to the extension 343 of the handle component 120 such that the plunger 341 is simultaneously actuated to push the inflation fluid from the syringe barrel 331 and into the balloon 112. In order to assure the release of the inflation fluid at an appropriate point in a procedure and to avoid accidental depression of the syringe plunger 341 prior thereto, the actuation cap 337 includes a pair of partial turn thread segments 338 extending from an inner surface thereof, as shown in FIG. 5, that mate with a corresponding pair of partial turn thread segments 339 on the extension 343 for locking a longitudinal position of the actuation cap 337 relative to the extension 343 and for thereby preventing unintended depression of the syringe plunger 341. When the thread segments 338, 339 are threadably engaged with each other, the inflation mechanism 110 is in a locked configuration. Further after a procedure when the balloon catheter 100 must be readied for removal, the inflation mechanism 110 in the unlocked configuration permits the actuation cap 337, and thereby the syringe plunger 341, to be proximally retracted relative to the handle component 120 and to thereby withdraw the inflation fluid and deflate the balloon 112. In embodiments in accordance herewith, each of the partial turn thread segments 338, 339 may be referred to as comprising a quarter turn of threads, and it should be understood by this description that the pair of partial turn thread segments 338 are spaced approximately 180 degrees from each other about the inner circumference of the actuation cap 337 and that the pair of partial turn thread segments 339 are spaced approximately 180 degrees from each other about the outer circumference of the extension 343 of the handle component 120.

With reference to FIG. 4, the outer surface or circumference of the extension 343 of the handle component 120 also includes a pair of opposing smooth surfaces or tracks 325 that are positioned between the pair of partial turn thread segments 339 so as to be spaced approximately 180 degrees from each other about the outer circumference of the extension 343. When actuation of the syringe plunger 341 is desired for releasing the inflation fluid from the syringe 333 or for withdrawing the inflation fluid from the balloon 112, the actuation cap 337 may be rotated approximately 90 degrees to disengage or unlock the pair of partial turn thread segments 338 thereof from the corresponding pair of partial turn thread segments 339 on the extension 343, and to thereby align the pair of partial turn thread segments 338 with the pair of tracks 325 of the extension 343. In such an orientation, the inflation mechanism 110 is in an unlocked configuration such that the actuation cap 337 may then be proximally or distally advanced relative to the extension 343 to thereby concurrently depress the syringe plunger 341 within the syringe barrel 331 to effectuate the release of the inflation fluid from the syringe 333 or to thereby retract the syringe plunger 341 relative to the syringe barrel 331 to effectuate the removal of the inflation fluid from the balloon 112. In embodiments hereof, the actuation cap 337 may at any time be rotated 90 degrees to re-engage the thread segments 338, 339, to thereby return the inflation mechanism to the locked configuration with the actuation cap 337 and the plunger 341 in a desired position, such as a position that prevents any potential push back by the inflated balloon so as to maintain a desired preselected or predetermined pressure therein. Accordingly, the inflation mechanism 110 is a self-contained feature of the handle component 120 and provides a fully complete inflation source for the balloon catheter 100 that is able to properly inflate the balloon 112 without the need for any other inflation fluid source or equipment. In another manner of description, the inflation mechanism 110 may be considered to constitute a complete and independent balloon inflation unit in and of itself.

In an embodiment hereof as noted above, the syringe 333 may be fluidly connected with the three-way connector 335 at the first proximal fitting 334. During operation, inflation fluid from the syringe 333 is received through the first proximal fitting 334 and delivered through the three-way connector 335 into the lumen 308 of the shaft component 102, where it is directed to the balloon 112 to provide inflation thereof. When inflation of the balloon 112 is desired, the actuation cap 337 is rotated so as to disengage the thread segments 338, 339, allowing the actuation cap 337 to depress the plunger 341 in the direction of the arrow A in FIGS. 3 and 6, forcing the inflation fluid in the syringe 333 to travel through first proximal fitting 334 and the three-way connector 335 into the shaft component lumen 308 and then into the balloon 112. In an embodiment, when the balloon 112 is inflated to a desired, preselected or set pressure the pressure relief valve 344 actuates and releases excess inflation fluid to ambient, thereby indicating to a clinician that the preselected pressure has been reached. In an embodiment, the preselected or predetermined pressure to which the balloon 112 may be inflated is 3 atmospheres such that the pressure relief valve 344 may be selected to release fluid at any pressure above 3 atmospheres so as to indicate when delivery of the inflation fluid to the balloon has reached the preselected pressure. In an embodiment, the pressure relief valve 344 is disposed within the handle component 120 to be in fluid communication with the proximal end 104 of the shaft component 102 and to be in fluid communication with a third distal fitting 345 of the three-way connector 335. Stated another way, the pressure relief valve 344 is situated upstream of and is fluidly coupled to the shaft component lumen 308 and the balloon 112, and is situated downstream of and is fluidly coupled to the distal fitting 345 of the three-way connector 335. In an embodiment, the pressure relief valve 344 may also be situated in a surface of the handle component 120 that is readily visible by a clinician so that any release of inflation fluid is readily visible as well.

Pressure relief valves adaptable for use in embodiments hereof may be purchased from the Qosina Company of Ronkonkoma, N.Y. Accordingly, the self-contained inflation mechanism 110 in combination with the built-in pressure relief valve 344 enables the handle component 120 to be utilized to properly inflate the balloon 112 of the balloon catheter 100 without the need for any other inflation fluid source or equipment and without additional pressure monitoring equipment.

Distal fitting 345 of the three-way connector 335 is also configured in the embodiment shown in FIG. 3 to provide a hub about which the distal knob 111 may be rotated. As well the three-way connector 335 of the handle component 120 includes a second proximal fitting 347 that is aligned with the distal fitting 345 along the longitudinal axis $L_A$ of the balloon catheter 100. The three-way connector 335 so situated within the handle component 120 slidably receives the elongated segment 240 of the needle component 230 through each of the second proximal fitting 347 and the distal fitting 345, and further is provided with a hemostatic valve (not shown) to assure hemostasis during a procedure utilizing the needle component 230. In an embodiment, a hemostatic seal (not shown) is embedded in the connector 335 such that the needle component 230 is forced through it to maintain a pressure (e.g., 3 ATMS) in the system distal thereof. In accordance with embodiments hereof, the handle component 102 and the various parts thereof may be molded articles of one or more suitable polymeric materials, such as acrylonitrile butadiene styrene (ABS), polycarbonate, acetal, etc.

In a method of forming a subintimal tract and positioning the balloon catheter 100 adjacent to the downstream end of an occlusion, the balloon catheter 100 is tracked over an indwelling guidewire through a prior formed subintimal tract until the tip component 118 of the catheter 100 is disposed at the distal side of the occlusion. Balloon 112 is then inflated, as described above, to anchor the catheter 100 within the subintimal tract. The needle component 230 is then advanced relative to the catheter 100, as described above, until the distal segment 242 of the needle component 230 distally extends from the tip component 118, or alternatively from a side port of the catheter 100, so as to thereafter be positioned to penetrate through the intima and to be passed into the true lumen of the vessel. A method of bypassing a vessel blockage may be performed in a proximal-to-distal direction, i.e. antegrade or with the blood flow, or in a distal-to-proximal direction, i.e. retrograde or against the blood flow if access is available from that direction. In other terms, the system and method described herein may be considered to bypass a vessel blockage from a near side of the blockage to a far side of the blockage.

Figure 7:
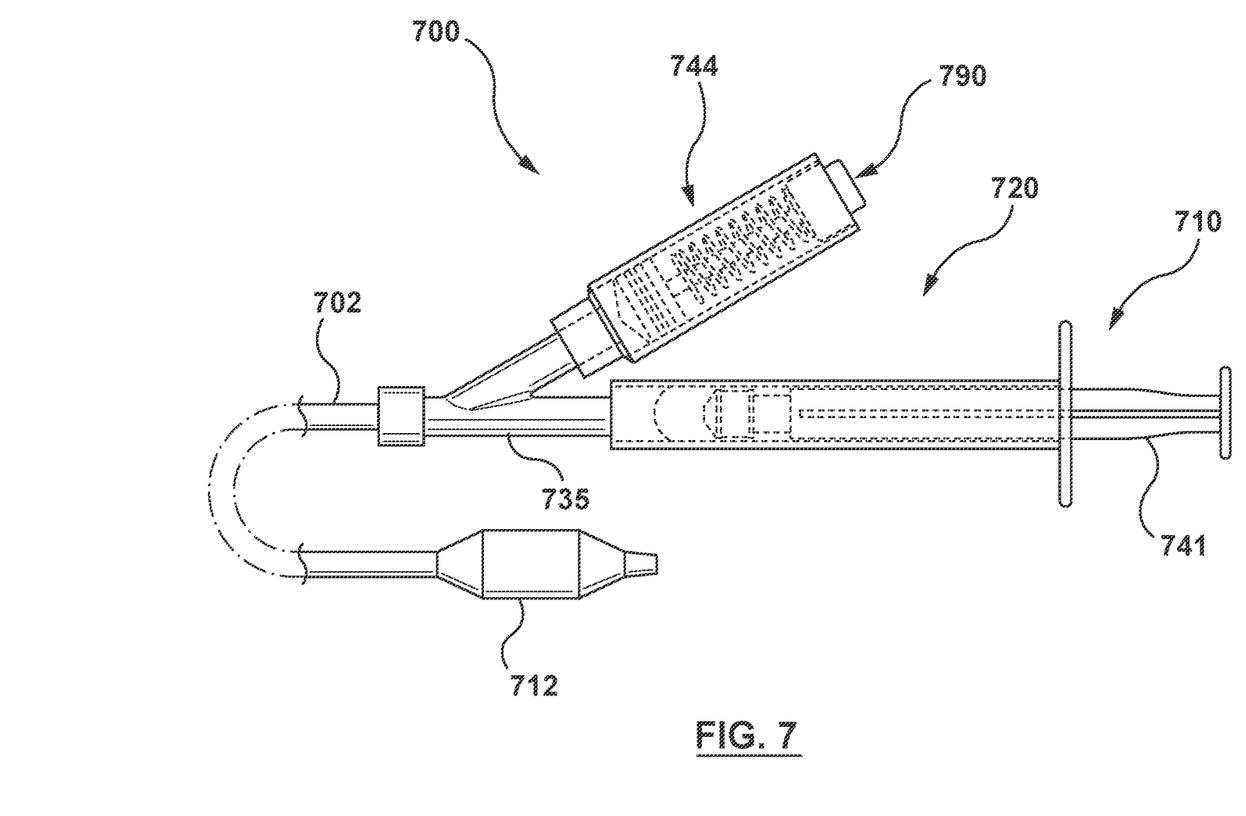
FIG. 7 is a side view of a balloon catheter with a handle component in accordance with another embodiment hereof.

In another embodiment, a balloon catheter 700 similar to the balloon catheter 100 may be used as a delivery catheter for deploying a balloon-expandable stent (not shown) within the vasculature or within another body lumen. In such an embodiment, a handle component 720 as shown in FIG. 7 may be attached to a proximal end of a shaft component 702 of the balloon catheter 700 to be in fluid communication with a balloon 712 thereof. The handle component 720 includes a self-contained inflation mechanism 710 in the form of a syringe that is in fluid communication with a pressure relief valve 744 of the handle component 720 via a connector 735. The pressure relief valve 744 and the inflation mechanism 710 are in fluid communication with an inflation lumen of the shaft component 702, via the connector 735 of the handle component 720, so as to thereby also be in fluid communication with the balloon 712. When inflation of the balloon 712 is desired, such as to deploy a balloon-expandable stent at a treatment site in vivo, a plunger 741 of the syringe 710 may be depressed to force an inflation fluid to be delivered to the balloon 712, via at least the connector 735 and the shaft component 702. In an embodiment, when the balloon 712 is inflated to a desired, preselected or set pressure the pressure relief valve 744 actuates such that a spring-loaded indicator 790 is pressed upward to alert a clinician that the preselected pressure has been reached. In an embodiment, the preselected or predetermined pressure to which the balloon 712 may be inflated before the pressure relief valve 744 is tripped or actuated may be in a range of between 0.1 atmospheres and 20 atmospheres. In another embodiment, the pressure relief valve 744 may be configured to release inflation fluid at the preselected or predetermined pressure to provide a readily visible indicator to a clinician and to thereby also prevent over-pressurization of the balloon.

Figure 8:
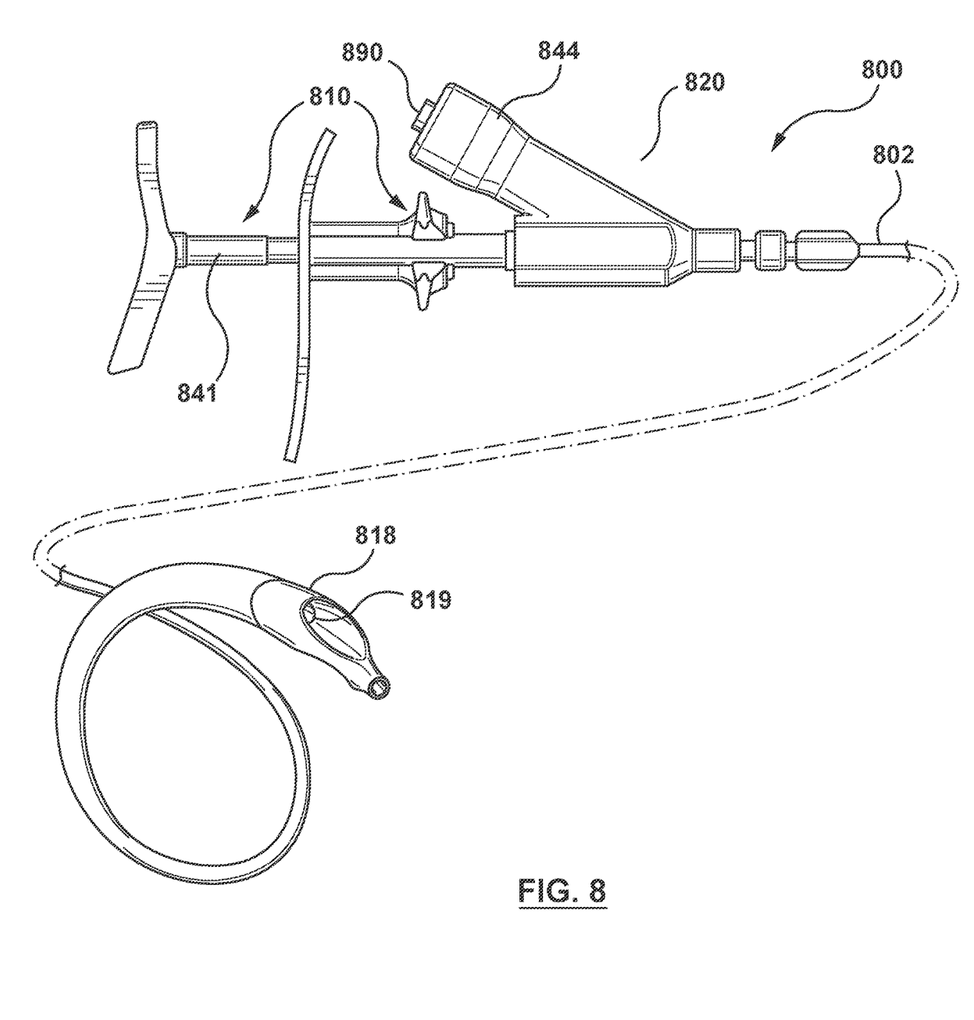
FIG. 8 is a side view of a delivery catheter with a handle component in accordance with another embodiment hereof.

In accordance with another embodiment hereof, a handle component 820 may form a component of a delivery catheter 800 for delivering a material to a treatment site in vivo. In an embodiment, the material may be a biocompatible foam or other substance and the treatment site may be an aneurysm to be filled with the foam or other substance in an aneurysmal sac filling therapy, which may be undertaken, for instance, to minimize or eliminate Type II endoleaks. In such an embodiment, the handle component 820 as shown in FIG. 7 may be attached to a proximal end of a shaft component 802 of the delivery catheter 800 to be in fluid communication with a distal tip 818 thereof. The handle component 820 includes a self-contained delivery mechanism 810 in the form of a syringe that contains or holds a material for delivery in vivo, such as a foam or other substance. As in the previous embodiments, the delivery mechanism 810 is in fluid communication with a pressure relief valve 844 of the handle component 820. The pressure relief valve 844 and the delivery mechanism 810 are in turn in fluid communication with a delivery lumen 819 of the shaft component 802, so as to thereby also be in fluid communication with the distal tip 818 of the delivery catheter 800. When a material contained in the delivery mechanism 810 of the handle component 820 is desired to be released, such as to be deployed within an enclosed cavity or aneurysm at a treatment site in vivo, a plunger 841 of the delivery mechanism or syringe 810 may be depressed to force the material to be delivered from the distal tip 818 of the delivery catheter 800 to the enclosed cavity or aneurysm. In an embodiment, when the enclosed cavity or aneurysm reaches a desired preselected pressure, the pressure relief valve 844 actuates such that a spring-loaded indicator 890 is pressed upward to alert a clinician that the preselected pressure has been reached. In an embodiment, a preselected or predetermined pressure that indicates the enclosed cavity or aneurysm has received a suitable quantity of the delivered material pressures will be low and in certain instances will be associated with the blood pressure of the patient. In an embodiment the preselected pressure will be sufficient to indicate that the fill material has compressed the thrombus in the aneurysmal sac so as to choke off any lumens that are formed in that thrombus. Accordingly, the pressure for such an embodiment will be rather low and may be in a range of between 10 mm and 50 mm of mercury, such that any pressure there above will trip or actuate the pressure relief valve 844. In another embodiment, the pressure relief valve 844 may be configured to release a delivery material at the preselected or predetermined pressure to provide a readily visible indicator to a clinician.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A handle component of a medical device for delivering a material to an enclosed cavity comprising:
    a self-contained mechanism for holding the material and for providing the material to the enclosed cavity, wherein the self-contained mechanism includes a syringe and an actuation cap that is coupled to a head of a plunger of the syringe, wherein the self-contained mechanism includes a locked configuration in which a longitudinal position of the actuation cap and the plunger is locked to thereby prevent movement of the plunger of the syringe relative to an extension of the handle component, wherein in the locked configuration the actuation cap is threadably engaged with the extension of the handle component; and
    a pressure relief valve in fluid communication with the self-contained mechanism and the enclosed cavity, the pressure relief valve being configured to indicate when delivery of the material to the enclosed cavity reaches a preselected pressure.

2. The handle component of claim 1, wherein the medical device is a balloon catheter, the material is an inflation fluid and the enclosed cavity is a balloon of the balloon catheter.

3. The handle component of claim 2, wherein the self-contained mechanism is in fluid communication with a lumen of the balloon catheter, and wherein the lumen is in fluid communication with the balloon.

4. The handle component of claim 3, wherein the syringe contains the inflation fluid for inflating the balloon to the preselected pressure when a plunger of the syringe is depressed.

5. The handle component of claim 4, wherein the preselected pressure is between 0.1 ATM and 20 ATM.

6. The handle component of claim 4, wherein the self-contained mechanism includes an unlocked configuration in which the actuation cap is configured to be distally advanced relative, to the extension of the handle component to thereby simultaneously depress the plunger of the syringe to release the inflation fluid therefrom for inflating the balloon.

7. The handle component of claim 6, wherein with the self-contained mechanism in the unlocked configuration the actuation cap is configured to be proximally retracted relative, to the handle component and to thereby simultaneously retract the plunger of the syringe to remove the inflation fluid and deflate the balloon.

8. The handle component of claim 1, wherein the medical device is a delivery catheter, the material is a foam and the enclosed cavity is an aneurysm.

9. The handle component of claim 8, wherein the self-contained mechanism is in fluid communication with a lumen of the delivery catheter, and wherein the lumen is configured to be in fluid communication with the aneurysm when the delivery catheter is deployed in vivo.

10. The handle component of claim 9, wherein the syringe includes the foam for filling the aneurysm to the preselected pressure when a plunger of the syringe is depressed.

11. The handle component of claim 10, wherein the preselected pressure is between 10 mm and 50 mm of mercury.

12. The handle component of claim 1, further comprising:
    a spring-loaded indicator coupled to the pressure relief valve, wherein the pressure relief valve is configured to indicate when delivery of the material to the enclosed cavity reaches a preselected pressure by moving the spring-loaded indicator in an upwards direction away from the handle component.

13. The handle component of claim 12, wherein the syringe of the self-contained mechanism has at least a portion thereof situated within the handle component.

14. The handle component of claim 13, wherein the syringe includes the material for filling the enclosed cavity to the preselected pressure when the plunger of the syringe is depressed.

15. The handle component of claim 14, wherein the material is an inflation, fluid and the enclosed cavity is a balloon of a catheter.

16. The handle component of claim 15, wherein a lumen of the catheter is configured to be in fluid communication with each of the syringe and the balloon when the catheter is deployed in vivo so as to receive the inflation fluid from the syringe and to deliver the inflation fluid to the balloon.

17. The handle component of claim 14, wherein the material is a foam and the enclosed cavity is an aneurysm.

18. The handle component of claim 17, wherein a lumen of a catheter is configured to be in fluid communication with each of the syringe and the aneurysm when the catheter is deployed in vivo so as to receive the foam from the syringe and to deliver the foam to the aneurysm.

19. The handle component of claim 1, wherein the extension of the handle component is configured to receive a barrel of the syringe and the actuation cap is configured to securely receive the head of the plunger of the syringe.

20. A handle component of a medical device for delivering a material to an enclosed cavity comprising:
a self-contained mechanism for holding the material and for providing the material to the enclosed cavity, wherein the self-contained mechanism includes a syringe and an actuation cap that is coupled to a head of a plunger of the syringe, wherein the self-contained mechanism includes a locked configuration in which a longitudinal position of the actuation cap and the plunger is locked to thereby prevent movement of the plunger of the syringe relative to an extension of the handle component, wherein in the locked configuration the actuation cap is threadably engaged with the extension of the handle component; and
a pressure relief valve in fluid communication with the self-contained mechanism and the enclosed cavity, the pressure relief valve being configured to indicate when delivery of the material to the enclosed cavity reaches a preselected pressure,
wherein the extension of the handle component includes a pair of partial turn thread segments on an outer surface thereof and a pair of smooth surfaces on the outer surface thereof, and the actuation cap includes a pair of partial turn thread segments on an inner surface thereof, the pair of partial turn thread segments of the actuation cap being configured to mate with the pair of partial turn thread segments of the extension of the handle component, and wherein the actuation cap is configured to be rotated to engage the pair of partial turn thread segments of the actuation cap with the pair of partial turn thread segments of the extension of the handle component to lock the self-contained mechanism and wherein the actuator cap is configured to be rotated to align the pair of partial turn thread segments of the actuation cap with the pair of smooth surfaces of the extension of the handle component to unlock the self-contained mechanism.

\* \* \* \* \*